US00PP21995P2

(12) United States Plant Patent
Strode

(10) Patent No.: US PP21,995 P2
(45) Date of Patent: Jun. 28, 2011

(54) ***COLOCASIA* PLANT NAMED 'MOJITO'**

(50) Latin Name: *Colocasia esculenta*
Varietal Denomination: Mojito

(75) Inventor: Ty Richard Strode, Altamonte Springs, FL (US)

(73) Assignee: Agri-Starts, Inc., Apopka, FL (US)

( * ) Notice: Subject to any disclaimer, the term of this patent is extended or adjusted under 35 U.S.C. 154(b) by 0 days.

(21) Appl. No.: 12/655,602

(22) Filed: Dec. 31, 2009

(51) Int. Cl.
*A01H 5/00* (2006.01)

(52) U.S. Cl. ..... Plt./373

(58) Field of Classification Search ..... Plt./263.1, Plt./226, 373
See application file for complete search history.

*Primary Examiner* — Susan B McCormick Ewoldt
(74) *Attorney, Agent, or Firm* — C. A. Whealy

(57) ABSTRACT

A new and distinct cultivar of *Colocasia* plant named 'Mojito', characterized by its tall and upright plant habit; vigorous growth habit; rapid growth rate; large ovate-shaped variegated leaves that are green, dark green and black in color; and red purple-colored leaf petioles with very dark-colored longitudinal streaks and stripes.

3 Drawing Sheets

Botanical designation: *Colocasia esculenta.*
Cultivar denomination: 'MOJITO'.

BACKGROUND OF THE INVENTION

The present invention relates to a new and distinct cultivar of *Colocasia* plant, botanically known as *Colocasia esculenta,* and hereinafter referred to by the name 'Mojito'.

The new *Colocasia* plant is a naturally-occurring branch mutation of *Colocasia esculenta* 'Midnight', disclosed in U.S. Plant Pat. No. 17,887. The new *Colocasia* plant was discovered and selected by the Inventor on a single plant of 'Midnight' within a population of plants of 'Midnight' in a controlled greenhouse environment in Apopka, Fla. in May, 2007.

Asexual reproduction of the new *Colocasia* plant by tissue culture in a controlled environment in Apopka, Fla. since Nov. 15, 2007 has shown that the unique features of this new *Colocasia* plant are stable and reproduced true to type in successive generations of asexual reproduction.

SUMMARY OF THE INVENTION

Plants of the new *Colocasia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Mojito'. These characteristics in combination distinguish 'Mojito' as a new and distinct cultivar of *Colocasia:*

1. Tall and upright plant habit.
2. Vigorous growth habit; rapid growth rate.
3. Large ovate-shaped variegated leaves that are green, dark green and black in color.
4. Red purple-colored leaf petioles with very dark-colored longitudinal streaks and stripes.

Plants of the new *Colocasia* differ from plants of the parent, 'Midnight', in the following characteristics:

1. Plants of the new *Colocasia* are more vigorous and grow faster than plants of 'Midnight'.
2. Plants of the new *Colocasia* are larger than plants of 'Midnight'.
3. Plants of the new *Colocasia* have larger leaves than plants of 'Midnight'.
4. Plants of the new *Colocasia* and 'Midnight' differ in leaf color as plants of 'Midnight' have black-colored leaves.
5. Plants of the new *Colocasia* and 'Midnight' differ in leaf petiole coloration as plants of 'Midnight' have black-colored leaf petioles.

Plants of the new *Colocasia* can be compared to plants of *Colocasia esculenta* 'Illustris', not patented. In side-by-side comparisons conducted in Apopka, Fla., plants of the new *Colocasia* differed primarily from plants of 'Illustris' in the following characteristics:

1. Plants of the new *Colocasia* and 'Illustris' differed in leaf color and color pattern as plants of 'Illustris' had leaves with green-colored venal areas and black-colored intervenal areas.
2. Plants of the new *Colocasia* and 'Illustris' differed in leaf petiole coloration as plants of 'Illustris' had blackish brown and green-colored leaf petioles.

BRIEF DESCRIPTION OF THE PHOTOGRAPHS

The accompanying photographs illustrate the overall appearance of the new *Colocasia* plant. These photographs show the colors as true as it is reasonably possible to obtain in colored reproductions of this type. Colors in the photographs may differ slightly from the color values cited in the detailed botanical description which accurately describe the colors of the new *Colocasia* plant.

The photograph on the first sheet is a side perspective view of a typical plant of 'Mojito' grown in a container.

The photograph on the second sheet is a close-up view of the upper surface of a typical leaf of 'Mojito'.

The photograph on the third sheet is a close-up view of typical leaf petioles of 'Mojito'.

DETAILED BOTANICAL DESCRIPTION

The aforementioned photographs and following observations and measurements describe plants grown in 20-cm containers in Apopka, Fla. during the summer in a polyethylene-covered shaded greenhouse in Apopka, Fla. under conditions and cultural practices which approximate those generally used in commercial *Colocasia* production. During the production of the plants, day temperatures ranged from 23° C. to 33° C. and night temperatures ranged from about 20° C. to 33° C. Plants were four months old when the photographs and the detailed description were taken. In the following description, color references are made to The Royal Horticultural Society Colour Chart, 2001 Edition, except where general terms of ordinary dictionary significance are used.

Botanical classification: *Colocasia esculenta* 'Mojito'.

Parentage: Naturally-occurring branch mutation of *Colocasia esculenta* 'Midnight', disclosed in U.S. Plant Pat. No. 17,887.

Propagation:

*Type.*—By tissue culture.

*Time to initiate roots, summer.*—About one week at 29° C.

*Time to initiate roots, winter.*—About two weeks at 20° C.

*Time to produce a rooted young plants, summer.*—About three weeks at 29° C.

*Time to produce a rooted young plants, winter.*—About four weeks at 20° C.

*Root description.*—Medium in thickness, fleshy; white in color.

*Rooting habit.*—Moderate branching; moderately dense.

Plant description:

*Plant type.*—Herbaceous perennial.

*Plant/growth habit.*—Upright and tall plant habit; inverted triangle; rapid growth rate; vigorous growth habit; suitable for 15-cm to 35-cm containers; leaf petioles basal and orientated mostly upright, leaning slightly outwardly with development.

*Plant height, from soil level to top of leaf plane.*—About 90 cm.

*Plant diameter or spread.*—About 90 cm.

Foliage description:

*Length.*—About 35 cm.

*Width.*—About 24 cm.

*Shape.*—Ovate.

*Apex.*—Acute to cuspidate.

*Base.*—Cordate to sagittate; peltate.

*Margin.*—Entire; flat to slightly curled.

*Texture, upper and lower surfaces.*—Smooth, glabrous.

*Venation pattern.*—Pinnate.

*Color.*—Developing leaves, upper and lower surfaces: Random and irregular spots, streaks and sectors of 191B and 193A. Fully expanded leaves, upper surface: Random and irregular spots, blotches, streaks and sectors of 147A, 146B and 202A; venation striped with close to 202A, 70C to 70D or 71A; at petiole attachment, close to 79A. Fully expanded leaves, lower surface: Random and irregular spots, streaks and sectors of 191B, 193A and 200B; venation, striped with close to 70C to 70D or 71A.

*Petiole.*—Aspect: Mostly erect, leaning slightly outwardly with development. Length: About 20 cm to 60 cm. Diameter, distal: About 4 cm to 6 cm. Diameter, proximal: About 6 cm to 8 cm. Texture: Smooth, glabrous. Color: Close to 71C to 71D blending with close to 71A; random longitudinal streaks and stripes, close to 202A.

*Wing.*—Length: About 23 cm to 33 cm. Diameter: About 1.4 cm to 2.8 cm. Texture: Smooth, glabrous. Color: Close to 71A or 70C to 70D.

Inflorescence description: Inflorescence initiation and development have not been observed on plants of the new *Colocasia.*

Disease/pest resistance: Plants of the new *Colocasia* have not been observed to be resistant to pathogens and pests common to *Colocasia.*

Temperature tolerance: Plants of the new *Colocasia* have been observed to be tolerant to temperatures ranging from about 1° C. to about 40° C.

It is claimed:

1. A new and distinct *Colocasia* plant named 'Mojito' as illustrated and described.

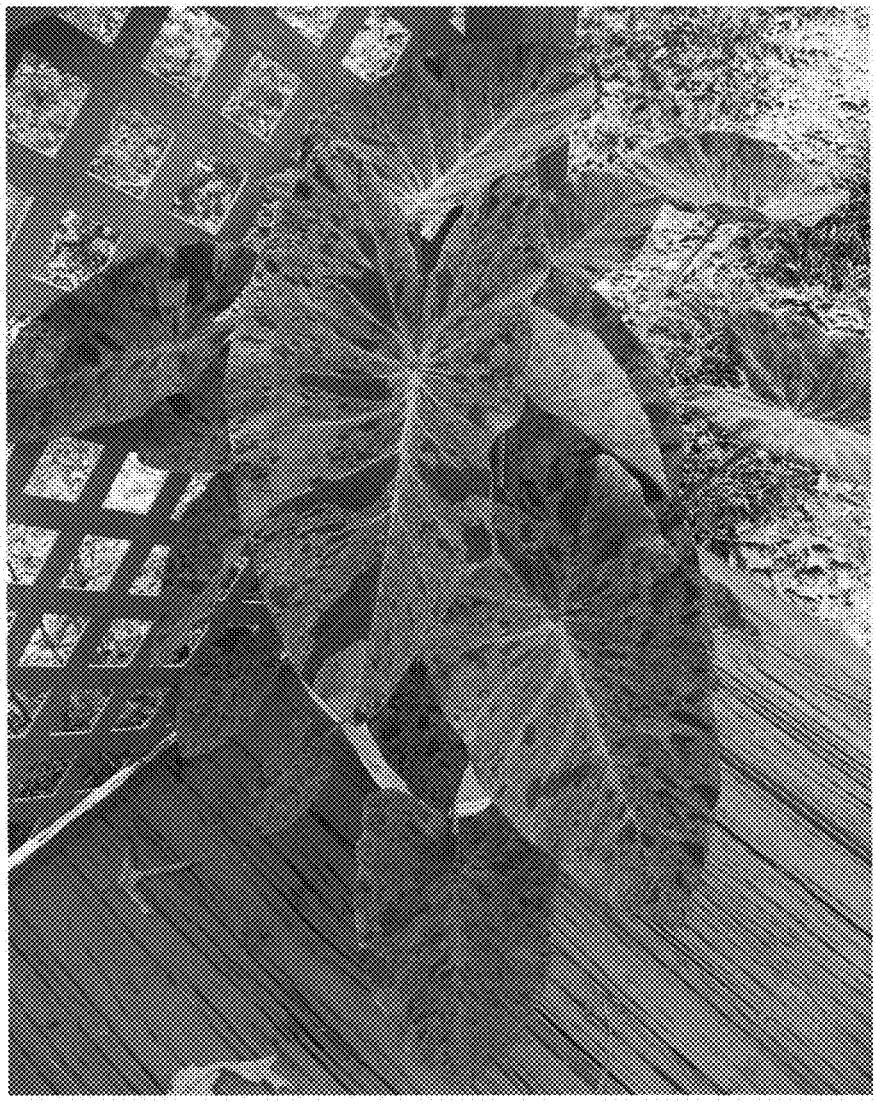

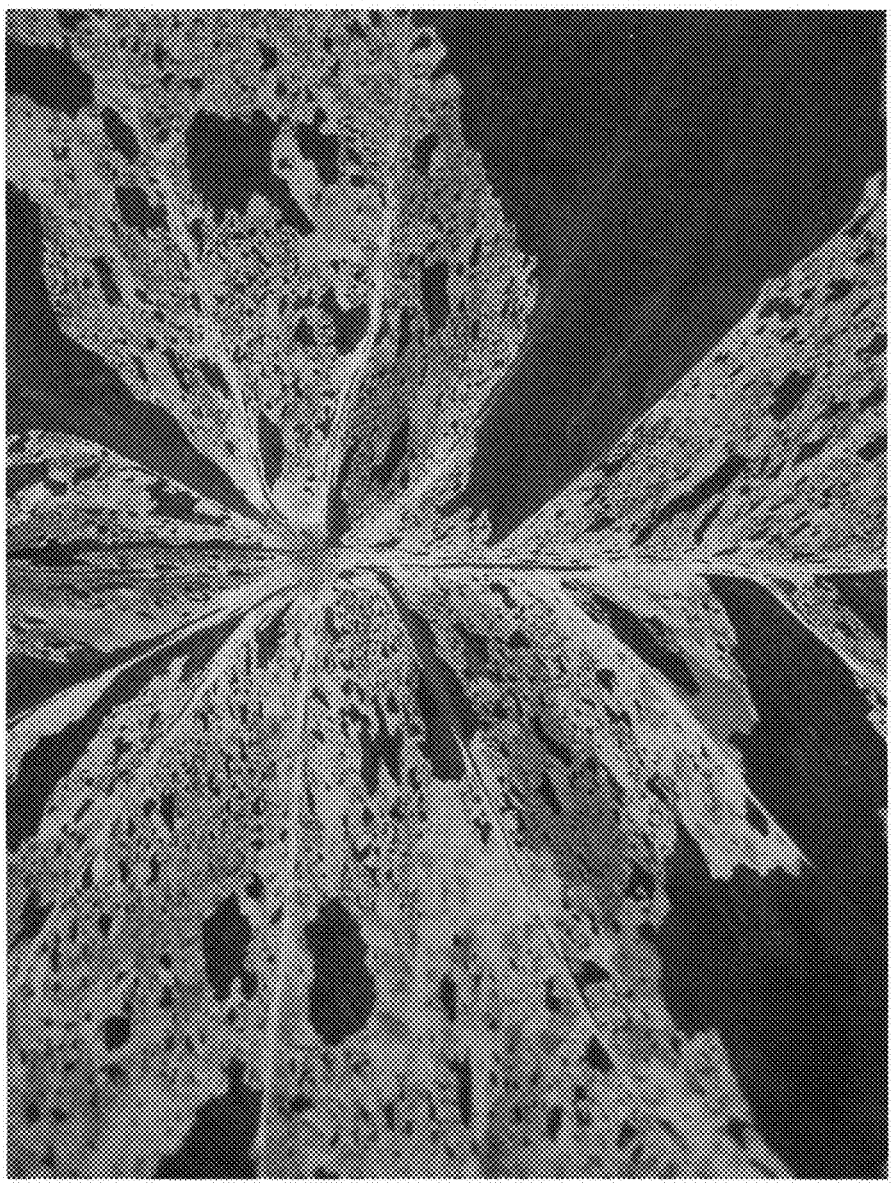

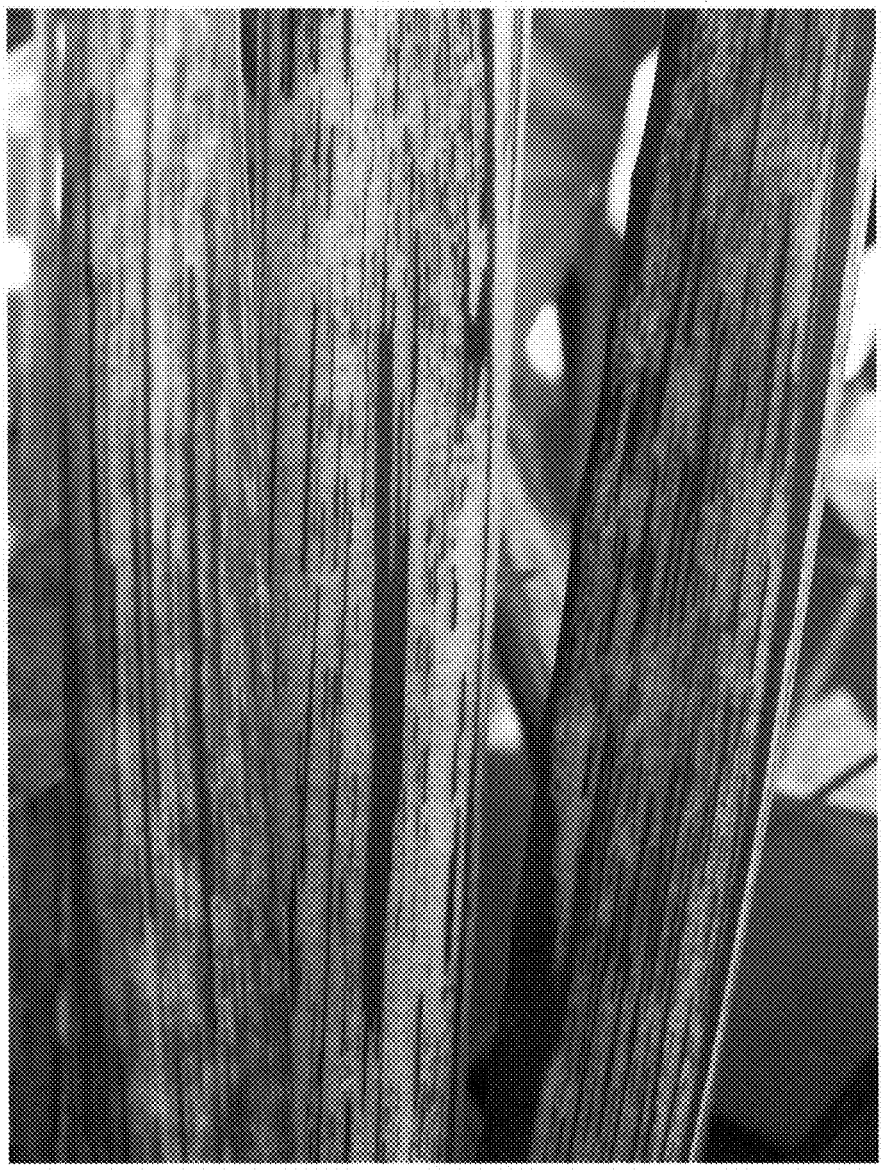

* * * * *